(12) United States Patent
Nishio

(10) Patent No.: US 11,039,852 B2
(45) Date of Patent: Jun. 22, 2021

(54) MEDICAL DEVICE

(71) Applicant: TERUMO KABUSHIKI KAISHA, Tokyo (JP)

(72) Inventor: Kousuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 196 days.

(21) Appl. No.: 16/351,625

(22) Filed: Mar. 13, 2019

(65) Prior Publication Data

US 2019/0209203 A1 Jul. 11, 2019

Related U.S. Application Data

(63) Continuation of application No. PCT/JP2017/032328, filed on Sep. 7, 2017.

(30) Foreign Application Priority Data

Sep. 16, 2016 (JP) .............................. JP2016-182402

(51) Int. Cl.
*A61B 17/3207* (2006.01)
*A61B 17/16* (2006.01)
(Continued)

(52) U.S. Cl.
CPC .. *A61B 17/320725* (2013.01); *A61B 17/1659* (2013.01); *A61B 17/32002* (2013.01);
(Continued)

(58) Field of Classification Search
CPC ...... A61B 17/320758; A61B 17/32075; A61B 2017/320766; A61B 2090/08021; A61B 17/32002; A61B 17/1659
See application file for complete search history.

(56) References Cited

U.S. PATENT DOCUMENTS 5,122,134 A * 6/1992 Borzone .............. A61B 17/164
606/80
5,584,843 A * 12/1996 Wulfman ....... A61B 17/320758
604/22
(Continued)

FOREIGN PATENT DOCUMENTS

JP     H09509605 A     9/1997

OTHER PUBLICATIONS

International Search Report (PCT/ISA/210) dated Nov. 21, 2017, by the Japanese Patent Office as the International Searching Authority for International Application No. PCT/JP2017/032328.
(Continued)

*Primary Examiner* — Richard G Louis
(74) *Attorney, Agent, or Firm* — Buchanan Ingersoll & Rooney PC

(57) ABSTRACT

A medical device is disclosed for cutting an object in a body lumen, including: a rotatable drive shaft; and a rotatable rotation structure which is connected to the drive shaft, the rotation structure including: a proximal portion; a distal portion; and a constricted portion provided between the proximal portion and the distal portion, the constricted portion including: a first tapered portion which includes a first cutting portion and decreases in diameter toward the distal side; a second tapered portion which includes a second cutting portion and decreases in diameter toward the proximal side; and a bottom portion which is provided between the first tapered portion and the second tapered portion.

20 Claims, 10 Drawing Sheets

(51) Int. Cl.
*A61B 17/32* (2006.01)
*A61B 90/00* (2016.01)

(52) U.S. Cl.
CPC .............. *A61B 17/320758* (2013.01); *A61B 17/32075* (2013.01); *A61B 2017/320766* (2013.01); *A61B 2090/08021* (2016.02)

(56) References Cited

U.S. PATENT DOCUMENTS

| | | | |
|---|---|---|---|
| 6,030,401 A * | 2/2000 | Marino | A61B 17/1671 606/170 |
| 6,565,588 B1 | 5/2003 | Clement et al. | |
| 6,579,298 B1 * | 6/2003 | Bruneau | A61B 17/320758 606/159 |
| 2008/0045986 A1 * | 2/2008 | To | A61B 17/320708 606/159 |
| 2014/0276840 A1 | 9/2014 | Richter et al. | |
| 2015/0141816 A1 * | 5/2015 | Gupta | A61B 5/0066 600/427 |

OTHER PUBLICATIONS

Written Opinion (PCT/ISA/237) dated Nov. 21, 2017, by the Japanese Patent Office as the International Searching Authority for International Application No. PCT/JP2017/032328.

* cited by examiner

MEDICAL DEVICE

CROSS-REFERENCES TO RELATED APPLICATIONS

This application is a continuation of International Application No. PCT/JP2017/032328 filed on Sep. 7, 2017, which claims priority to Japanese Application No. 2016-182402 filed on Sep. 16, 2016, the entire content of both of which is incorporated herein by reference.

TECHNICAL FIELD

The present disclosure generally relates to a medical device.

BACKGROUND DISCUSSION

Treatments for a body lumen (intravascular) against arteriosclerosis, atherectomy which cuts a stenotic object (object) formed by thrombus, plaque, calcified lesion, and the like are known. Atherectomy is an important treatment for improving arterial patency after treatment. As the atherectomy, a method of cutting and removing a stenotic object by bringing a rotation body into contact with the stenotic body is mainly adopted nowadays (for example, see U.S. Pat. No. 6,565,588).

Conventionally, a device for cutting a stenotic object by pressing a catheter including a distal portion rotating at a high speed against the stenotic object is developed as a device for atherectomy. However, in the press type device, when a catheter is pressed against a stenotic object, the catheter may be bent in a blood vessel and hence a force may not be easily transmitted to the stenotic object. For that reason, a rigid stenotic object (lesions) such as calcified lesions may not be cut by the press type device.

Therefore, there is a demand for a device capable of cutting a stenotic object with a strong pulling force when pulling a catheter in order to more efficiently cutting rigid lesions such as calcified lesions. Further, at this time, there is a demand for reducing the risk of damaging a biological tissue such as a normal blood vessel wall along with the function of cutting rigid lesions.

SUMMARY

A medical device is disclosed, which is capable of reducing the risk of damaging a biological tissue while cutting a rigid stenotic object inside a body lumen.

A medical device according to an embodiment of the present disclosure is a medical device for cutting an object in a body lumen, including: a rotatable drive shaft; and a rotatable rotation structure which is connected to the drive shaft, the rotation structure including: a proximal portion; a distal portion; and a constricted portion provided between the proximal portion and the distal portion, the constricted portion including: a first tapered portion which includes a first cutting portion and decreases in diameter toward the distal side; a second tapered portion which includes a second cutting portion and decreases in diameter toward the proximal side; and a bottom portion which is provided between the first tapered portion and the second tapered portion.

According to an embodiment of the present disclosure, the bottom portion of the constricted portion preferably has a diameter smaller than a maximum diameter of the proximal portion and a maximum diameter of the distal portion.

According to an embodiment of the present disclosure, the first tapered portion preferably has a maximum diameter larger than a maximum diameter of the second tapered portion.

According to an embodiment of the present disclosure, the first cutting portion is preferably a surface of the first tapered portion.

According to an embodiment of the present disclosure, the second cutting portion is preferably a surface of the second tapered portion.

According to an embodiment of the present disclosure, the distal portion preferably has a diameter smaller than a diameter of the proximal portion.

According to an embodiment of the present disclosure, the angle of the second tapered portion with respect to a cross-section orthogonal to a rotation axis of the rotation structure is preferably equal to or smaller than the angle of the first tapered portion with respect to the cross-section.

According to an embodiment of the present disclosure, the distal portion is preferably a non-cutting portion capable of smoothly coming into contact with a biological tissue.

According to an embodiment of the present disclosure, the medical device preferably further includes a third tapered portion which is provided on a side more distal than the distal portion and decreases in diameter toward the distal side, and the third tapered portion preferably includes a third cutting portion.

According to an embodiment of the present disclosure, the medical device preferably further includes a tubular outer sheath, which covers the outside of the drive shaft, and the outer sheath is preferably bendable.

According to an embodiment of the present disclosure, the first tapered portion preferably has a maximum diameter larger than the outer diameter of the outer sheath.

According to the medical device of the present disclosure, the risk of damaging a biological tissue while cutting a rigid stenotic object inside a body lumen can be reduced.

In accordance with an aspect, a medical device for cutting an object in a body lumen, the medical device comprising: a rotatable drive shaft; and a rotatable rotation structure configured to be connected to the drive shaft, the rotatable rotation structure including: a proximal portion; a distal portion; and a constricted portion provided between the proximal portion and the distal portion, the constricted portion including: a first tapered portion having a first cutting portion, the first tapered portion decreasing in diameter toward the distal side; a second tapered portion having a second cutting portion, the second portion decreasing in diameter toward the proximal side; and a bottom portion provided between the first tapered portion and the second tapered portion.

In accordance with another aspect, a medical device for cutting an object in a body lumen, the medical device comprising: a rotatable drive shaft; a rotatable rotation structure configured to be connected to the drive shaft, the rotation structure including: a proximal portion, the proximal portion including a cylindrical member and a plurality of connecting members surrounding the cylindrical member, each of the plurality of connecting member includes a hole portion configured to receive a bearing; a distal portion; and a constricted portion provided between the proximal portion and the distal portion, the constricted portion being separable from the proximal portion, and wherein the constricted portion includes: a first tapered portion having a first cutting portion, the first tapered portion decreasing in diameter toward the distal side; a second tapered portion having a second cutting portion, the second portion decreasing in diameter toward the proximal side; and a bottom portion provided between the first tapered portion and the second tapered portion; and one or more rings configured to surround the plurality of connecting members and the proximal portion of the rotatable rotation structure.

In accordance with a further aspect, a method for cutting substances inside a body lumen using a medical device including a rotatable drive shaft, and a rotatable rotation structure configured to be connected to the drive shaft, the rotation structure including: a proximal portion, a distal portion, and a constricted portion provided between the proximal portion and the distal portion, the constricted portion includes a first tapered portion having a first cutting portion, the first tapered portion decreasing in diameter toward the distal side, a second tapered portion having a second cutting portion, the second portion decreasing in diameter toward the proximal side, and a bottom portion provided between the first tapered portion and the second tapered portion, the method comprising: inserting the rotatable rotation structure into the body lumen; moving the rotatable rotation structure in a distal direction; and cutting the substances inside the body lumen with the rotatable rotation structure during the movement of the rotatable rotation structure in the distal direction.

BRIEF DESCRIPTION OF THE DRAWINGS

FIG. 5A illustrates a state in which a stenotic object is cut while the medical device is press-inserted and FIG. 5B illustrates a state in which the stenotic object is cut while the medical device is pulled.

DESCRIPTION OF EMBODIMENTS

Figure 1:
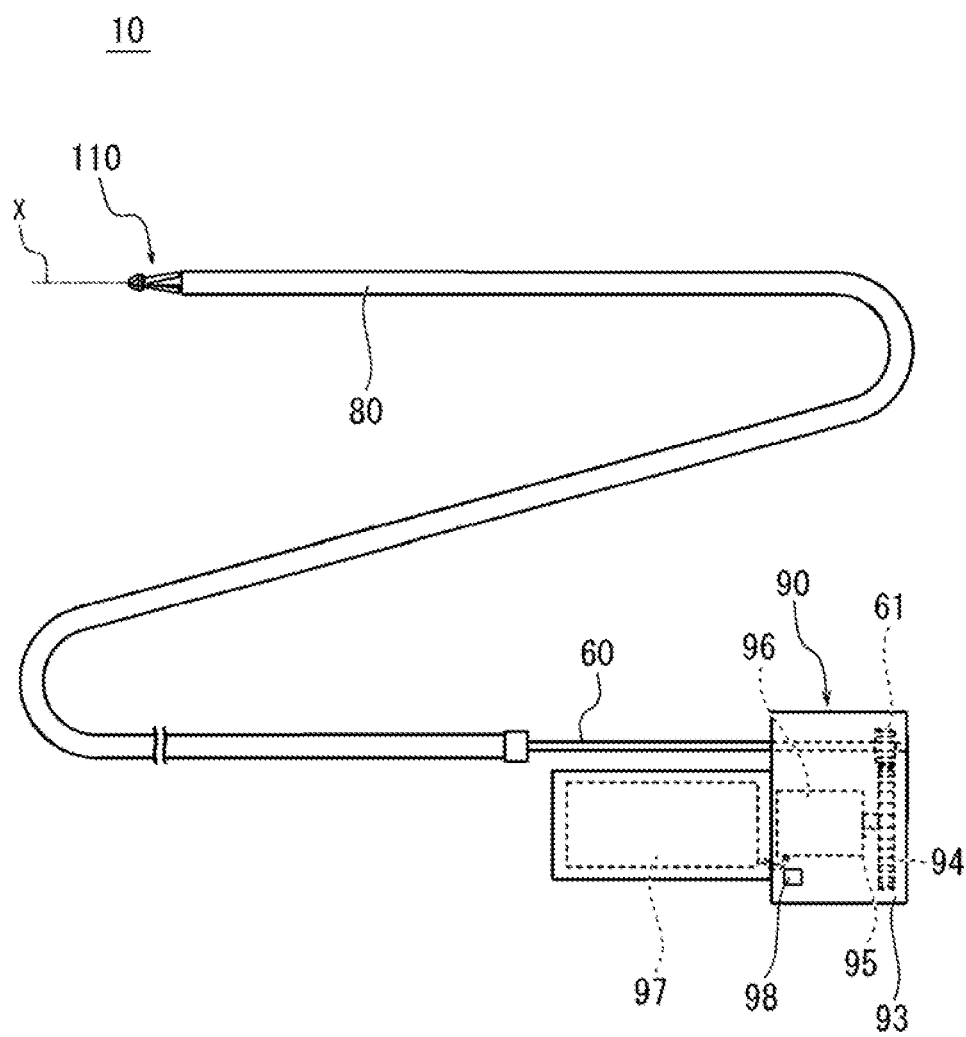
FIG. 1 is a diagram illustrating a medical device according to an embodiment of the present disclosure.

Hereinafter, an embodiment of the present disclosure will be described with reference to the drawings. Dimension ratios in the drawings may be exaggerated and may differ from actual ratios for convenience of description. Further, in each drawing, common members are denoted by the same reference numerals. Further, in this specification, the side to be inserted into the blood vessel of the medical device will be referred to as the "distal side" and the side to be operated will be referred to as the "proximal side".

Figure 2:
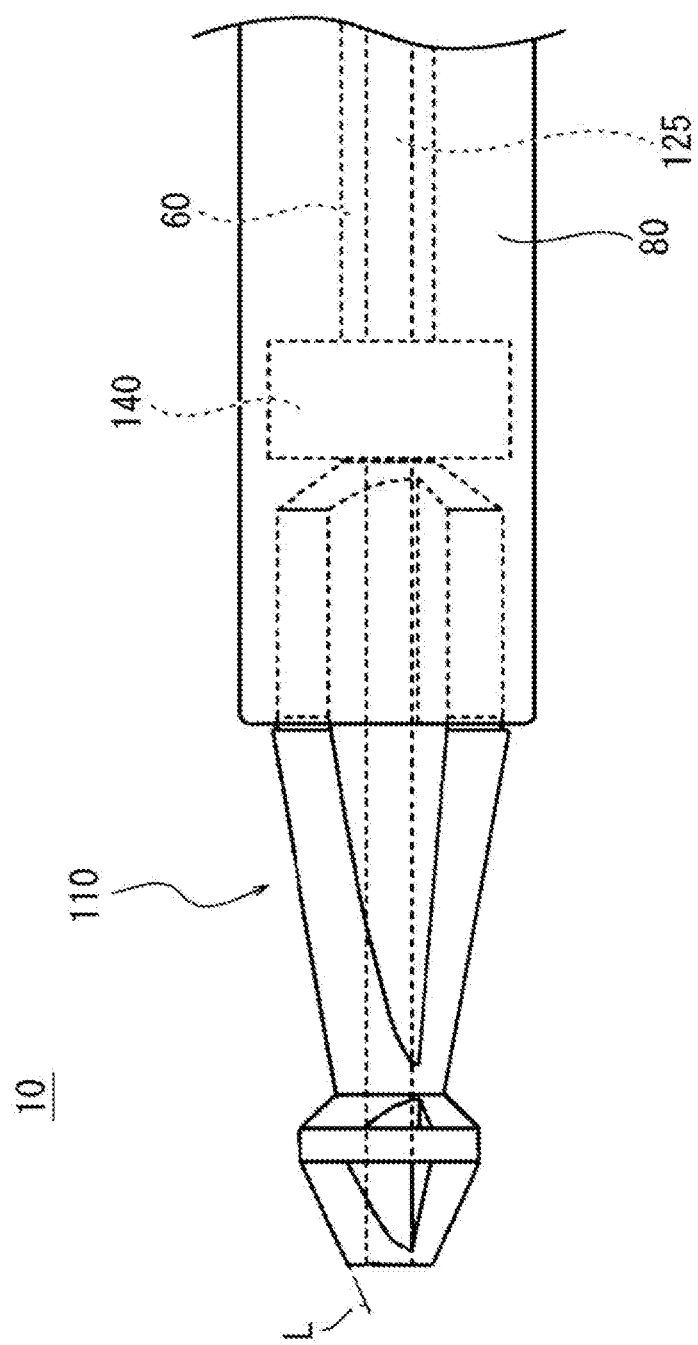
FIG. 2 is an enlarged plan view of a distal side of the medical device illustrated in FIG. 1.
Figure 3:
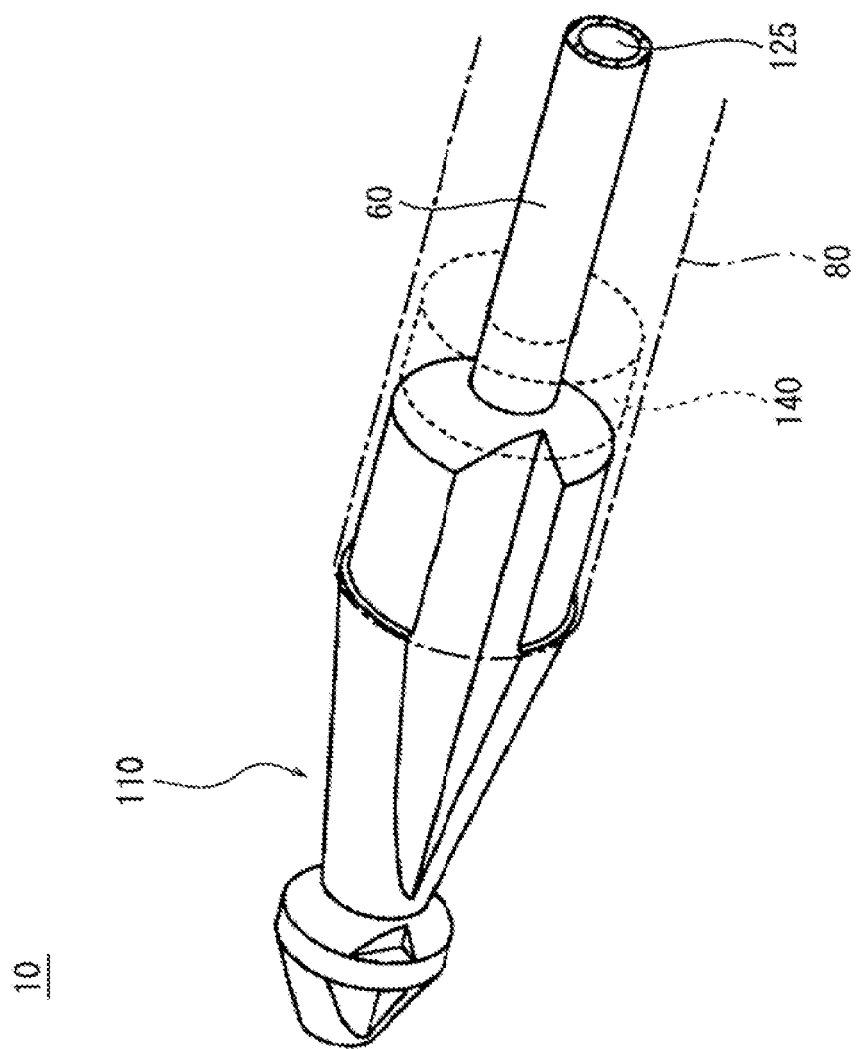
FIG. 3 is an enlarged perspective view of a distal side of the medical device illustrated in FIG. 1.

First, a configuration of a medical device according to an embodiment of the present disclosure will be described with reference to FIGS. 1 to 3. FIG. 1 is a diagram illustrating a medical device 10 according to an embodiment of the present disclosure. FIG. 2 is an enlarged plan view of the distal side of the medical device 10 illustrated in FIG. 1. FIG. 3 is an enlarged perspective view of the distal side of the medical device 10 illustrated in FIG. 1.

In accordance with an exemplary embodiment, the medical device 10 is used in a treatment of cutting an object inside a body lumen, for example, a treatment of cutting a stenotic object caused by plaque and thrombus inside a blood vessel. Next, a case of cutting a stenotic object inside a blood vessel will be described as an exemplary example.

In accordance with an exemplary embodiment, the medical device 10 includes, as illustrated in FIG. 1, a rotation structure 110 which is rotatable along a rotation axis X and is able to cut a stenotic object, a drive shaft 60 which drives the rotation of the rotation structure 110, an outer sheath 80 which is able to accommodate the rotation structure 110, and an operation unit 90 which operates the rotation structure 110 and the drive shaft 60.

As illustrated in FIGS. 2 and 3, the rotation structure 110 is connected to the drive shaft 60 and is driven by the drive shaft 60 when the drive shaft 60 rotates so that the rotation structure 110 rotates. The rotation of the drive shaft 60 is controlled by the operation unit 90 illustrated in FIG. 1. As illustrated in FIGS. 2 and 3, a bearing 140 is provided between the drive shaft 60 and the outer sheath 80. Since the bearing 140 is provided, the drive shaft 60 and the rotation structure 110 are smoothly rotatable with respect to the outer sheath 80.

A detailed structure of the rotation structure 110 will be described later.

In accordance with an exemplary embodiment, the drive shaft 60 is formed in a tubular shape. As illustrated in FIG. 1, the distal side of the drive shaft 60 is fixed to the rotation structure 110 and the proximal side of the drive shaft 60 is fixed to the driven gear 61 inside the operation unit 90.

In accordance with an exemplary embodiment, the drive shaft 60 is flexible and has a characteristic in which a rotational force exerted at the proximal side is transmitted to the distal side. The drive shaft 60 has, for example, a configuration in which a reinforcement member such as a wire formed of polyolefin such as polyethylene and polypropylene, polyamide, polyester such as polyethylene terephthalate, fluorine-based polymer such as ETFE, polyetheretherketone (PEEK), polyimide, or a combination of polyolefin, polyamide, polyester fluorine-based polymer, polyetheretherketone (PEEK), and/or polyimide is buried in a multi-layer coiled tubular body such as a three-layered coil wound alternately at the right and left sides in the winding direction.

The inner diameter of the drive shaft 60 can be appropriately selected, for example, the inner diameter of the drive shaft 60 can be 0.4 mm to 1.6 mm and can be set to 0.7 mm as an example. The outer diameter of the drive shaft 60 can be appropriately selected, for example, the outer diameter of the drive shaft 60 can be 0.6 mm to 1.6 mm and can be set to 1.0 mm as an example.

A guide wire lumen 125 into which a guide wire 130 (see FIGS. 5A, 5B, and 6 for the guide wire 130) is insertable is provided inside the drive shaft 60. The guide wire 130 is used to guide the rotation structure 110 when advancing the rotation structure 110 inside a blood vessel.

In accordance with an exemplary embodiment, the outer sheath 80 is a tubular body which covers the outside of the drive shaft 60 and is movable and rotatable in a direction along the rotation axis X with respect to the drive shaft 60. The outer sheath 80 can be operated while the proximal portion is gripped, can accommodate the rotation structure 110 in the outer sheath 80 while being moved to the distal side, and can expose a part of the rotation structure 110 to the outside while being moved to the proximal side. Further, the inner diameter of the outer sheath 80 can be smaller than a maximum diameter of a first tapered portion 116. For that reason, since the inner diameter of the outer sheath 80 is smaller than the maximum diameter of the first tapered portion 116, it is possible to further transmit a force in which the rotation structure 110 presses the intravascular wall by the outer sheath 80, it is possible to effectively perform a cutting operation.

The material, which forms the outer sheath 80 is not particularly limited, for example, the material of the outer sheath 80 can be polyolefins such as polyethylene and polypropylene, polyamides, polyesters such as polyethylene terephthalate, fluorine polymers such as ETFE, polyetheretherketone (PEEK), polyimide, and the like can be suitably used. Further, the outer sheath 80 may be formed of a plurality of materials or a reinforcement member such as a wire may be buried in the outer sheath 80.

The inner diameter of the outer sheath 80 can be appropriately selected, for example, the inner diameter of the outer sheath 80 can be 1.2 mm to 2.5 mm and can be set to 1.8 mm as an example. The outer diameter of the outer sheath 80 can be appropriately selected, for example, the outer diameter of the outer sheath 80 can be 1.3 mm to 2.6 mm and can be set to 2.0 mm as an example.

The operation unit 90 includes, as illustrated in FIG. 1, a drive mechanism 93 which applies a rotational force to the drive shaft 60.

In accordance with an exemplary embodiment, the drive mechanism 93 can include a drive gear 94 which meshes with the driven gear 61, a motor 96 which is a drive source including a rotation axis 95 to which the drive gear 94 is fixed, a battery 97 which is a battery or the like supplying electric power to the motor 96, and a switch 98 which controls the driving of the motor 96. When the rotation axis 95 of the motor 96 is rotated by turning on the switch 98, the driven gear 61 meshing with the drive gear 94 rotates and the drive shaft 60 rotates. When the drive shaft 60 rotates, the rotation structure 110 fixed to the distal side of the drive shaft 60 rotates.

Figure 4:
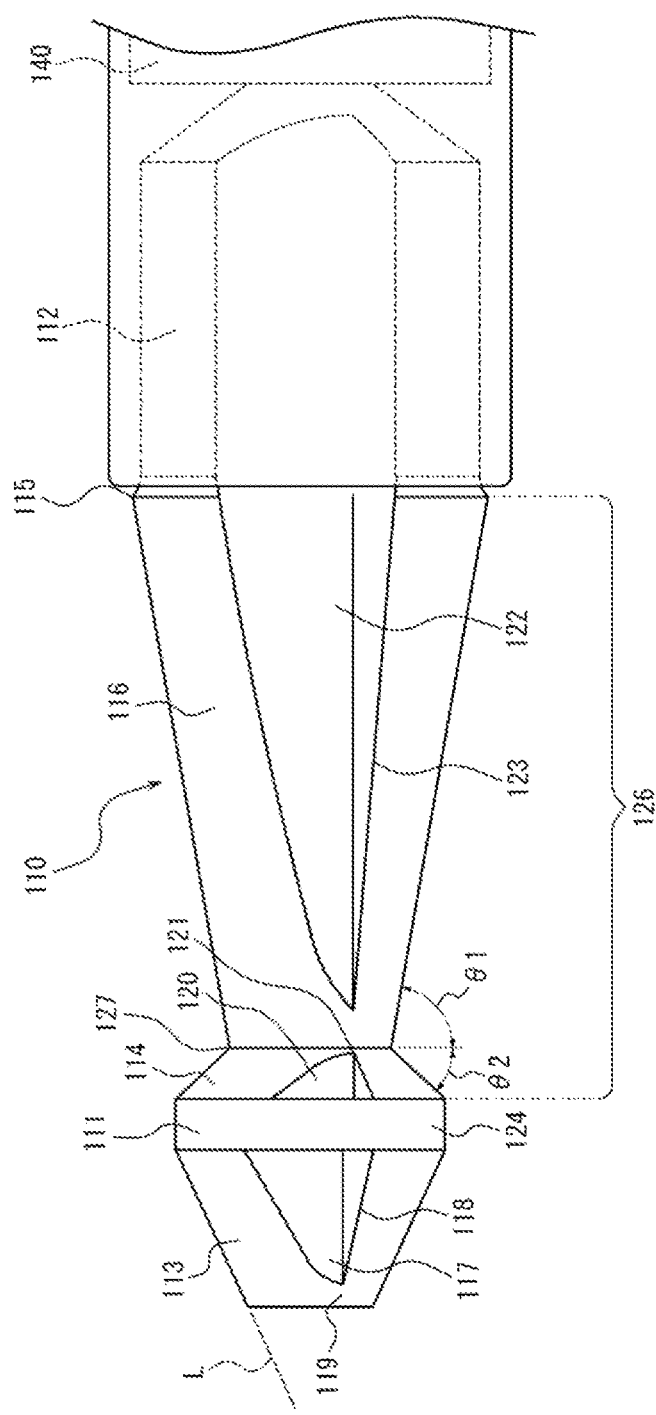
FIG. 4 is an enlarged plan view of a part including a rotation structure of FIG. 2.

Subsequently, a structure of the rotation structure 110 will be described with reference to FIG. 4. FIG. 4 is an enlarged plan view of a part including the rotation structure 110 of FIG. 2. In the description below, the "distal side" means the distal side of the rotation structure 110 and the "proximal side" means the proximal side of the rotation structure 110.

In accordance with an exemplary embodiment, the rotation structure 110 includes a first annular portion (a proximal portion) 112 and a second annular portion (a distal portion) 111 which is located on a side more distal than (i.e., distally of) the first annular portion 112. Further, the rotation structure 110 includes a constricted portion 126, which is provided between the first annular portion 112 and the second annular portion 111. In the rotation structure 110 of the embodiment, a step portion 115 of which a diameter increases in a step shape at the distal side is provided between the first annular portion 112 and the constricted portion 126. The first annular portion 112 may be a proximal end of the first tapered portion 116. The second annular portion 111 may be a distal end of a second tapered portion 114.

The constricted portion 126 includes the first tapered portion 116 which is provided at the distal side of the first annular portion 112 decreasing in diameter toward the distal side and the second tapered portion 114 which is provided at the proximal side of the second annular portion 111 decreasing in diameter toward the proximal side. The first tapered portion 116 of the embodiment decreases in diameter from the step portion 115 toward the distal side. Further, the second tapered portion 114 of the embodiment decreases in diameter from the second annular portion 111 toward the proximal side. The rotation structure 110 of the embodiment has a structure which includes the above-described step portion 115 and in which the first tapered portion 116 decreases in diameter from the step portion 115 toward the distal side, but may have a structure which does not include the step portion 115 and in which the first tapered portion 116 decreases in diameter from the first annular portion 112 toward the distal side. Further, the constricted portion 126 includes a bottom portion (i.e., lower inner edge) 127 which is provided between the first tapered portion 116 and the second tapered portion 114. The diameter of the bottom portion 127 is smaller than the diameter of the first annular portion 112 and the diameter of the second annular portion 111. Here, the "diameter" means a diameter about the rotation axis of the rotation structure 110. Further, the term "diameter" is not a term used only when the cross-section orthogonal to the rotation axis is circular. When the cross-section orthogonal to the rotation axis is not circular, a circular locus, which is depicted by a portion farthest from the rotation axis of the cross-section about the rotation axis, is described as the term "diameter". The same also applies to the description below. The shape of the constricted portion 126 may be formed by the first tapered portion 116 and the second tapered portion 114 having the same maximum diameter. Further, the shape of the constricted portion 126 may be formed by the first tapered portion 116 and the second tapered portion 114 of which the maximum diameter is larger than that of the first tapered portion 116. Further, the shape of the constricted portion 126 may be formed by the first tapered portion 116 of which the maximum diameter is larger than that of the second tapered portion 114 and the second tapered portion 114. The axial length of the constricted portion 126 may be formed by the first tapered portion 116 and the second tapered portion 114 having the same axial length. The axial length of the constricted portion 126 may be formed by the first tapered portion 116 of which the axial length is longer than that of the second tapered portion 114 and the second tapered portion 114. The axial length of the constricted portion 126 may be formed by the first tapered portion 116 and the second tapered portion 114 of which the axial length is longer than that of the first tapered portion 116.

Further, the rotation structure 110 includes a third tapered portion 113 which is provided at the distal side of the second annular portion 111 decreasing in diameter toward the distal side.

In accordance with an exemplary embodiment, the first tapered portion 116 includes a first notch portion 122 which is provided in a part of the circumferential portion to be notched in a V shape in a cross-section orthogonal to the axis and a first cutting portion 123, which is a blade, is provided at the edge portion of the first notch portion 122. The first notch portion 122 may be provided only at one position or two or more positions in the circumferential portion. The first notch portion 122 and the first cutting portion 123 may be formed to be continuous to, as illustrated in FIG. 4, the step portion 115 and the first annular portion 112. The first notch portion 122 may be asymmetric or symmetric. In the first notch portion 122, an angle of a surface of the first notch portion 122 opposite to the rotation direction of the rotation structure 110 is larger than that of a surface of the first notch portion 122 in the rotation direction. In accordance with an exemplary embodiment, abrasive grains, grinding stones, or the like (i.e., an abrasive material) may be electrodeposited on the first tapered portion 116. In the case where the first tapered portion 116 has, for example, abrasive grains, grinding stones or the like on the first tapered portion 116, the first tapered portion 116 becomes a fourth cutting portion. When the first tapered portion 116 includes the first cutting portion 123 of the first notch portion 122 and the first cutting portion (the fourth cutting portion) having abrasive grains, grinding stones, or the like electrodeposited on first cutting portion 123 (the fourth cutting portion), it is possible to efficiently cut a stenotic object by the first cutting portion 123 of the first notch portion 122 and the first cutting portion (the fourth cutting portion) having abrasive grains, grinding stones, or the like electrodeposited on the first cutting portion (the fourth cutting portion). Further, the first tapered portion 116 may not include the first notch portion 122, but may include only the fourth cutting portion, i.e., the first tapered portion 166 having the abrasive grains, grinding stones, and the like. In accordance with an exemplary embodiment, abrasive grains can be, for example, diamond abrasive grains or the like.

In accordance with an exemplary embodiment, the second tapered portion 114 includes a second notch portion 120 which is provided in a part of the circumferential portion to be notched in a V shape in a cross-section orthogonal to the axis and a second cutting portion 121, which is a blade, is provided at the edge portion of the second notch portion 120. The second notch portion 120 may be provided only at one position or two or more positions in the circumferential portion. The second notch portion 120 may be asymmetric or symmetric. In the second notch portion 120, an angle of a surface of the second notch portion 120 opposite to the rotation direction of the rotation structure 110 is larger than an angle of a surface of the second notch portion 120 in the rotation direction. Further, abrasive grains, grinding stones, or the like may be electrodeposited on the second tapered portion 114. In that case, the second tapered portion 114 with the abrasive grains, grinding stones, or the like becomes a fifth cutting portion. When the second tapered portion 114 includes the second cutting portion 121 of the second notch portion 120 and the fifth cutting portion having abrasive grains, grinding stones, or the like electrodeposited on the second cutting portion 121 (the fifth cutting portion), it is possible to efficiently cut a stenotic object by the second cutting portion 121 of the second notch portion 120 and the second cutting portion 121 (the fifth cutting portion) having abrasive grains, grinding stones, or the like electrodeposited on the second cutting portion 121 (the fifth cutting portion). Further, the second tapered portion 114 may not include the second notch portion 120, but may include only the fifth cutting portion. In accordance with an exemplary embodiment, abrasive grains can be, for example, diamond abrasive grains or the like.

In accordance with an exemplary embodiment, the third tapered portion 113 includes a third notch portion 117 which is provided in a part of the circumferential portion to be notched in a V shape in a cross-section orthogonal to the axis and a third cutting portion 118, which is a blade, is provided at the edge portion of the third notch portion 117. The third notch portion 117 may be provided only at one position or two or more positions in the circumferential portion. The third notch portion 117 may be asymmetric or symmetric. In the third notch portion 117, an angle of a surface of the third notch portion 117 opposite to the rotation direction of the rotation structure 110 is larger than that of the third notch portion 117 in the rotation direction. Further, abrasive grains, grinding stones, or the like may be electrodeposited on the third tapered portion 113. In that case, the third tapered portion 113 with the abrasive grains, grinding stones, or the like becomes a sixth cutting portion. When the third tapered portion 113 includes the third cutting portion 118 of the third notch portion 117 and the sixth cutting portion having abrasive grains, grinding stones, or the like electrodeposited on the third cutting portion (the sixth cutting portion), it is possible to efficiently cut a stenotic object by the third cutting portion 118 of the third notch portion 117 and the third cutting portion (the sixth cutting portion) having abrasive grains, grinding stones, or the like electrodeposited on the third cutting portion (the sixth cutting portion). Further, the third tapered portion 113 may not include the third notch portion 117, but may include only the sixth cutting portion. In accordance with an exemplary embodiment, abrasive grains can be, for example, diamond abrasive grains or the like.

In accordance with an exemplary embodiment, since the first cutting portion 123 and the third cutting portion 118 are formed in a tapered part which decreases in diameter toward the distal side, it is possible to effectively cut the stenotic object when pressing the rotation structure 110 toward the distal side. Further, since the second cutting portion 121 is formed in a tapered part, which decreases in diameter toward the proximal side, it is possible to effectively cut the stenotic object when pulling the rotation structure 110 toward the proximal side. In accordance with an exemplary embodiment, the axial lengths of the first notch portion 122, the second notch portion 120, and the third notch portion 117 are respectively proportional to the axial lengths of the first tapered portion 116, the second tapered portion 114, and the third tapered portion 113.

The first tapered portion 116 and the second tapered portion 114 are connected to each other by the bottom portion (i.e., lower inner edge) 127 so that an outer peripheral surface has a V shape in a longitudinal section passing through the center axis. In accordance with an exemplary embodiment, when an angle 81 of the first tapered portion 116 with respect to a cross-section orthogonal to the axis is compared with an angle 82 of the second tapered portion 114 with respect to a cross-section orthogonal to the axis, the angle 82 is equal to or smaller than the angle 81. For this reason, it can be relatively easy to hook the second cutting portion 121 to the stenotic object when pulling and cutting the stenotic object.

The second annular portion 111 may be constructed of such a shape and material that an outer peripheral surface of the second annular portion 111 can relatively smoothly come into contact with biological tissues. For example, when the outer peripheral surface of the second annular portion 111 is constructed of the shape and material that the second annular portion 111 can relatively smoothly come into contact with the biological tissues (i.e., non-cutting purpose), the second annular portion 111 can include a first non-cutting portion 124. Accordingly, it is possible to reduce the risk of damaging the biological tissue when cutting the stenotic object. Further, the third tapered portion 113 may be provided with a second non-cutting portion 119 in which the third notch portion 117 is not formed on the outer peripheral surface of the distal side end portion throughout the entire area in the circumferential portion. In this way, since the third cutting portion 118 does not protrude outward in relation to the tangent line L between the first non-cutting portion 124 and the second non-cutting portion 119, it is possible to prevent the third cutting portion 118 from coming into contact with biological tissues and to secure relatively high safety.

The material, which forms the rotation structure 110 is not particularly limited, for example, the rotation structure material can be stainless steel, Ta, Ti, Pt, Au, W, Ni, NiTi alloy, super steel (WC), high speed (HSS), polyolefins such as polyethylene and polypropylene, polyamides, polyesters such as polyethylene terephthalate, fluorine polymers such as PTFE, polyetheretherketone (PEEK), polyimide, and the like can be appropriately used.

In the medical device 10 according to the embodiment, the rotation structure 110 includes the constricted portion 126, the constricted portion 126 includes the second tapered portion 114 which decreases in diameter toward the proximal side, and the second tapered portion 114 includes the second cutting portion 121. In accordance with an exemplary embodiment, when the second cutting portion 121 is provided in the second tapered portion 114, which decreases in diameter toward the proximal side, the medical device 10 according to the embodiment can cut a stenotic object inside a body lumen when pulling the rotation structure 110. At this time, since a relatively strong force can be applied to the stenotic object by pulling the rotation structure 110, the medical device 10 according to the embodiment can cut the rigid stenotic object inside the body lumen. Further, at this time, since the diameter of the bottom portion 127 of the constricted portion 126 is smaller than the diameter of the first annular portion 112 and the diameter of the second annular portion 111, the risk of damaging a biological tissue such as a normal blood vessel can be reduced.

Further, in the embodiment, the diameter of the second annular portion 111 is smaller than the diameter of the first annular portion 112. Accordingly, the rotation structure 110 can be rather smoothly pressed during the pressing operation. Further, when the medical device 10 has a function of suctioning the stenotic object cut by the rotation structure 110 from a gap between the rotation structure 110 and the outer sheath 80, it is possible to rather efficiently suction the cut stenotic object since the diameter of the second annular portion 111 is smaller than the diameter of the first annular portion 112.

Further, in the embodiment, an angle of the second tapered portion 114 with respect to a cross-section orthogonal to the rotation axis of the rotation structure 110 is equal to or smaller than an angle of the first tapered portion 116 with respect to the cross-section. Accordingly, it is rather easy to hook the second cutting portion 121 to the stenotic object when pulling the rotation structure 110 and cutting the stenotic object.

Further, in the embodiment, the rotation structure 110 further includes the third tapered portion 113 which decreases in diameter from the second annular portion 111 toward the distal side and the third tapered portion 113 includes the third cutting portion 118. Accordingly, the stenotic object can be cut relatively evenly by the third cutting portion 118 when pressing the rotation structure 110 and the rotation structure 110 can be relatively smoothly pressed (or pushed) toward the distal side.

Figure 5A:
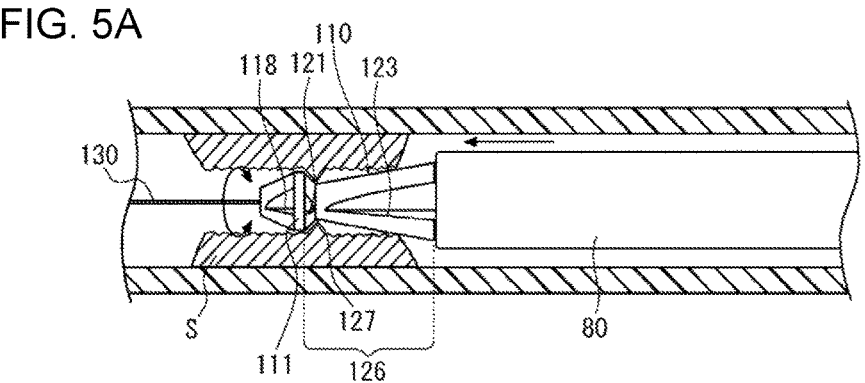
FIGS. 5A and 5B are schematic cross-sectional views illustrating a state inside a blood vessel when a procedure is performed by using the medical device illustrated in FIG. 1, where
Figure 5B:
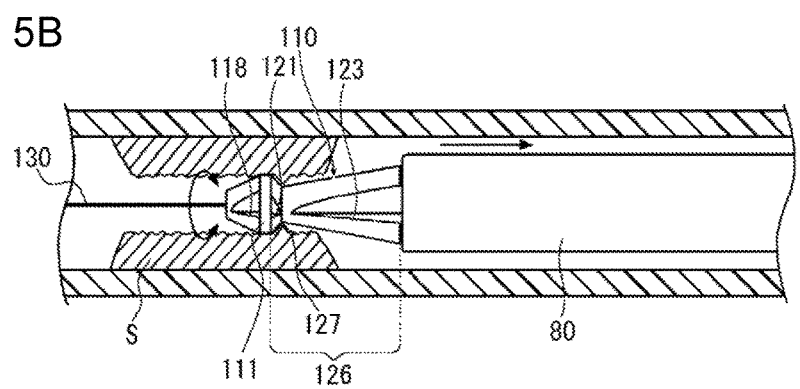

FIGS. 5A and 5B illustrate a state in which a stenotic object S inside a blood vessel is cut by using the medical device 10 according to an exemplary embodiment. FIG. 5A illustrates a state in which the stenotic object is cut by pressing the rotation structure 110 and FIG. 5B illustrates a state in which the stenotic object is cut by pulling the rotation structure 110.

As illustrated in FIG. 5A, the rotation structure 110 is first inserted into the blood vessel when pressing the rotation structure 110 and cutting the stenotic object S. Next, when the drive shaft 60 (see FIGS. 2 and 3) is rotated, the rotation structure 110 rotates and hence the stenotic object S inside the body lumen can be cut by the third cutting portion 118 and the first cutting portion 123. At this time, since the diameter of the bottom portion 127 of the constricted portion 126 is smaller than the diameter of the first annular portion 112 (see FIG. 4) and the diameter of the second annular portion 111, the first cutting portion 123 can be prevented from coming into contact with biological tissues such as normal blood vessels and relatively high safety can be secured.

Further, as illustrated in FIG. 5B, when the drive shaft 60 is rotated when pulling the rotation structure 110 and cutting the stenotic object S, the rotation structure 110 rotates and hence the stenotic object S inside the body lumen can be cut by the second cutting portion 121. At this time, since the diameter of the bottom portion 127 of the constricted portion 126 is smaller than the diameter of the first annular portion 112 and the diameter of the second annular portion 111, the second cutting portion 121 can be prevented from coming into contact with biological tissues such as normal blood vessels and relatively high safety can be secured. Although an unevenness remains on the surface of the stenotic object S due to various factors (factors on whether the stenotic object S is rigid, the rotation of the rotation structure 110 is biased, and the like) just by pressing the rotation structure 110 toward the distal side, the unevenness of the stenotic object S can be reduced by pulling the rotation structure 110 toward the proximal side and cutting the stenotic object S by the second cutting portion 121 inside the constricted portion 126.

Figure 6:
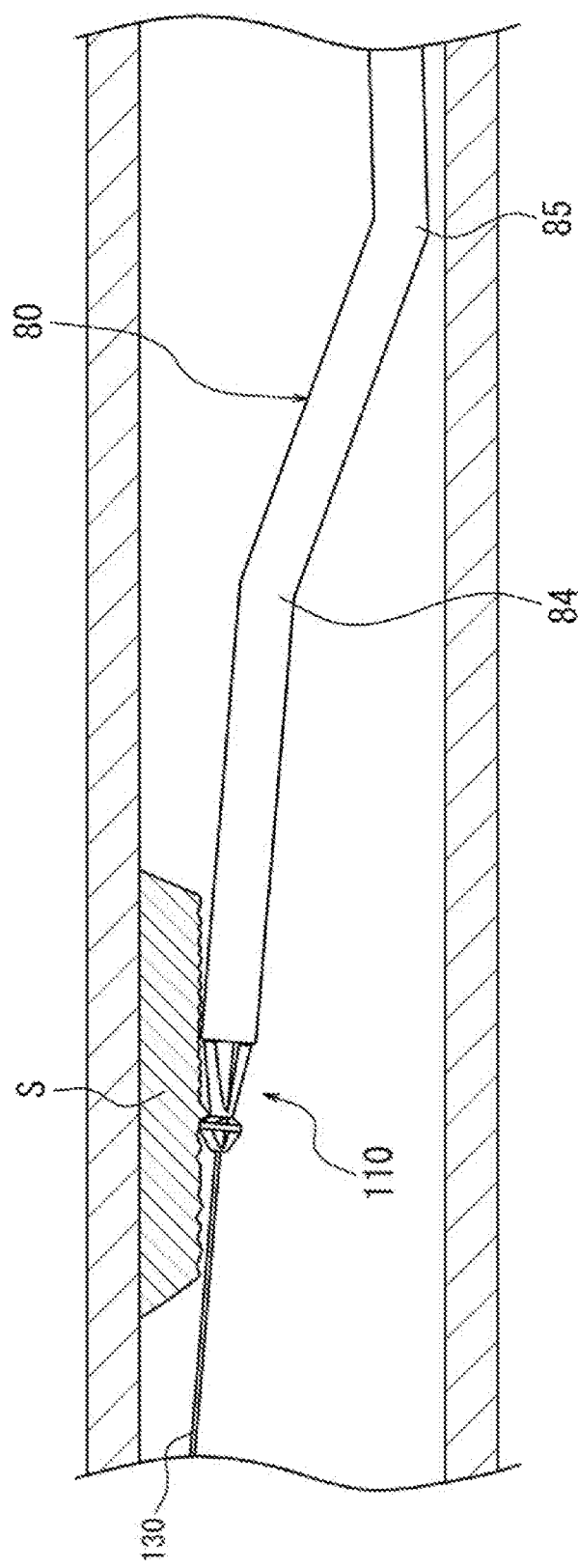
FIG. 6 is a schematic cross-sectional view illustrating a state inside a blood vessel when a procedure is performed by using the medical device illustrated in FIG. 1 while an outer sheath is bent.

FIG. 6 illustrates a state in which the outer sheath 80 of the medical device 10 is bent and the stenotic object S is cut. The outer sheath 80 is bendable as illustrated in FIG. 6. Here, the bendable state means a state in which an object can be bent and a state in which an object is bent.

In the example illustrated in FIG. 6, the outer sheath 80 is bent at two positions of the first curved portion 84 and the second curved portion 85. In accordance with an exemplary embodiment, the stenotic object S that is the cutting target can be accurately cut by bending the outer sheath 80 so that the rotation structure 110 comes into contact with the stenotic object S that is the cutting target and the risk of damaging biological tissues such as normal blood vessels can be reduced.

Hereinafter, three examples (Procedures 1 to 3) will be described as an example of a procedure using the medical device 10.

Procedure 1

First, the guide wire 130 is inserted into a blood vessel and is disposed in a lesion area. Next, the medical device 10 is disposed in the lesion area along the guide wire 130. The constricted portion 126 of the medical device 10 is pressed against the lesion area so that the lesion area enters the constricted portion 126 and at least one of the second tapered portion 114, the second notch portion 120, and the second cutting portion 121 is brought into contact with the stenotic object. The stenotic object is cut by at least one of the second tapered portion 114, the second notch portion 120, and the second cutting portion 121 by moving the rotation structure 110 of the medical device 10 in the proximal direction in a rotation state. After the stenotic part is cut, the medical device 10 and the guide wire 130 are extracted from the blood vessel.

Procedure 2

First, the guide wire 130 is inserted into a blood vessel and is disposed in a lesion area. Next, the medical device 10 is disposed in the lesion area along the guide wire 130. The stenotic object is pressed by the third tapered portion 113 of the medical device 10. Then, the stenotic object is cut by at least one of the third tapered portion 113, the third notch portion 117, and the third cutting portion 118 while the rotation structure 110 of the medical device 10 is rotated and moved in the distal direction. After the medical device 10 is moved to a certain extent in the distal direction, the constricted portion 126 is pressed against the lesion area so that the lesion area enters the constricted portion 126 and at least one of the second tapered portion 114, the second notch portion 120, and the second cutting portion 121 is brought into contact with the stenotic object. The stenotic object is cut by at least one of the second tapered portion 114, the second notch portion 120, and the second cutting portion 121 by moving the rotation structure 110 of the medical device 10 in the proximal direction in a rotation state. The cutting operation may be performed by repeating the movement of the medical device 10 in the distal direction and the proximal direction. After the stenotic part is cut, the medical device 10 and the guide wire 130 are extracted from the blood vessel.

Procedure 3

First, the guide wire 130 is inserted into a blood vessel and is disposed in a lesion area. Next, the medical device 10 is disposed in the lesion area along the guide wire 130. The stenotic object is pressed by the third tapered portion 113 of the medical device 10. Then, the stenotic object is cut by at least one of the third tapered portion 113, the third notch portion 117, and the third cutting portion 118 while moving the medical device 10 in the distal direction. The medical device 10 is moved in the distal direction in this state so that the stenotic object cut by the third tapered portion 113 is further cut by at least one of the first tapered portion 116, the first notch portion 122, and the first cutting portion 123 having a diameter larger than that of the third tapered portion 113. After the medical device 10 is moved in the distal direction to a certain extent, the constricted portion 126 is pressed against the lesion area so that the lesion area enters the constricted portion 126 and at least one of the second tapered portion 114, the second notch portion 120, and the second cutting portion 121 is brought into contact with the stenotic object. When the rotation structure 110 of the medical device 10 is moved in the proximal direction in a rotation state, the stenotic object is cut by at least one of the second tapered portion 114, the second notch portion 120, and the second cutting portion 121. After the stenotic part is cut, the medical device 10 and the guide wire 130 are extracted from the blood vessel.

Modified Example

Figure 7:
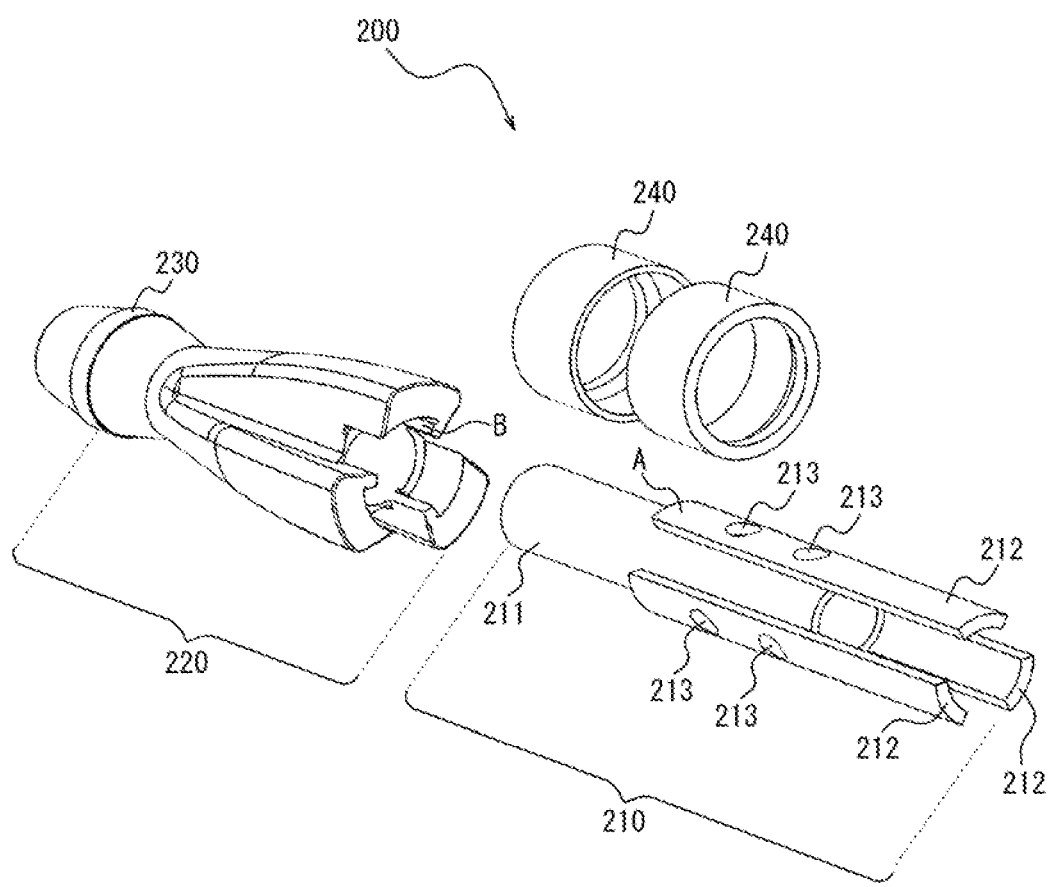
FIG. 7 is an exploded perspective view of a rotation structure according to a modified example.
Figure 8:
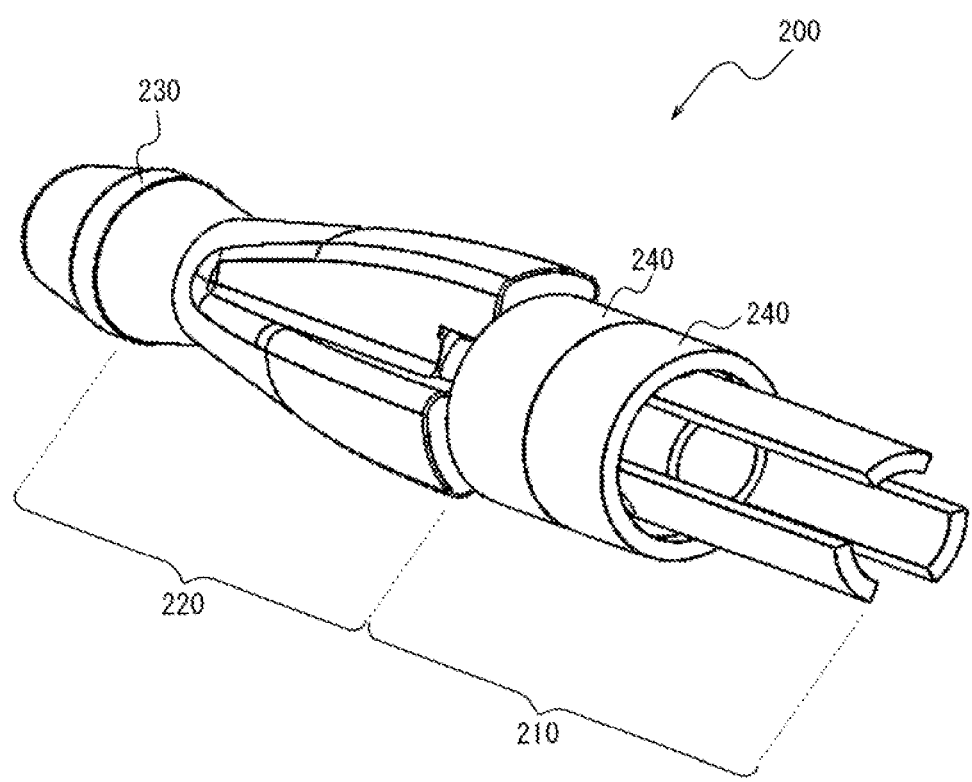
FIG. 8 is a perspective view of the rotation structure according to the modified example.

A configuration of a rotation structure according to a modified example of the present disclosure will be described with reference to FIGS. 7 and 8. FIG. 7 is an exploded perspective view of a rotation structure 200 according to the modified example. FIG. 8 is a perspective view of the rotation structure 200 according to the modified example.

In accordance with an exemplary embodiment, the rotation structure 200 includes, as illustrated in FIG. 8, a proximal portion 210, a constricted portion 220, a distal portion 230, and a ring 240. As illustrated in FIG. 7, the rotation structure 200 is mainly different from the rotation structure 110 illustrated in FIGS. 2 to 4 in that the proximal portion 210 and the constricted portion 220 are separated from each other.

In accordance with an exemplary embodiment, the proximal portion 210 includes, as illustrated in FIG. 7, a cylindrical member 211 and three connecting members 212 surrounding the cylindrical member 211.

The connecting member 212 includes a hole portion 213. A ball (or balls), for example, for a ball bearing can be inserted into the hole portion 213 and the ball bearing includes the ball and the ring 240.

Although not illustrated in FIGS. 7 and 8, the distal end surface of the drive shaft 60 adheres to the proximal end surface of the cylindrical member 211. Further, the outer surface of the drive shaft 60 adheres to each of the inner surfaces of three connecting members 212.

Accordingly, the connecting member 212 rotates when the drive shaft 60 rotates. Since the distal part A of the connecting member 212 illustrated in FIG. 7 is fitted to a concave portion B of the constricted portion 220, the constricted portion 220 and the distal portion 230 rotate when the connecting member 212 rotates.

With such a configuration, the rotation structure 200 is strong against a torque load and a bending load.

The disclosure is not limited to the above-described embodiment and can be modified into various forms by the person skilled in the art within the technical spirit of the disclosure. For example, the body lumen into which the medical device is inserted is not limited to the blood vessel, for example, the body lumen can be a vascular tube, a ureter, a bile duct, a fallopian tube, or a hepatic duct.

Figure 9:
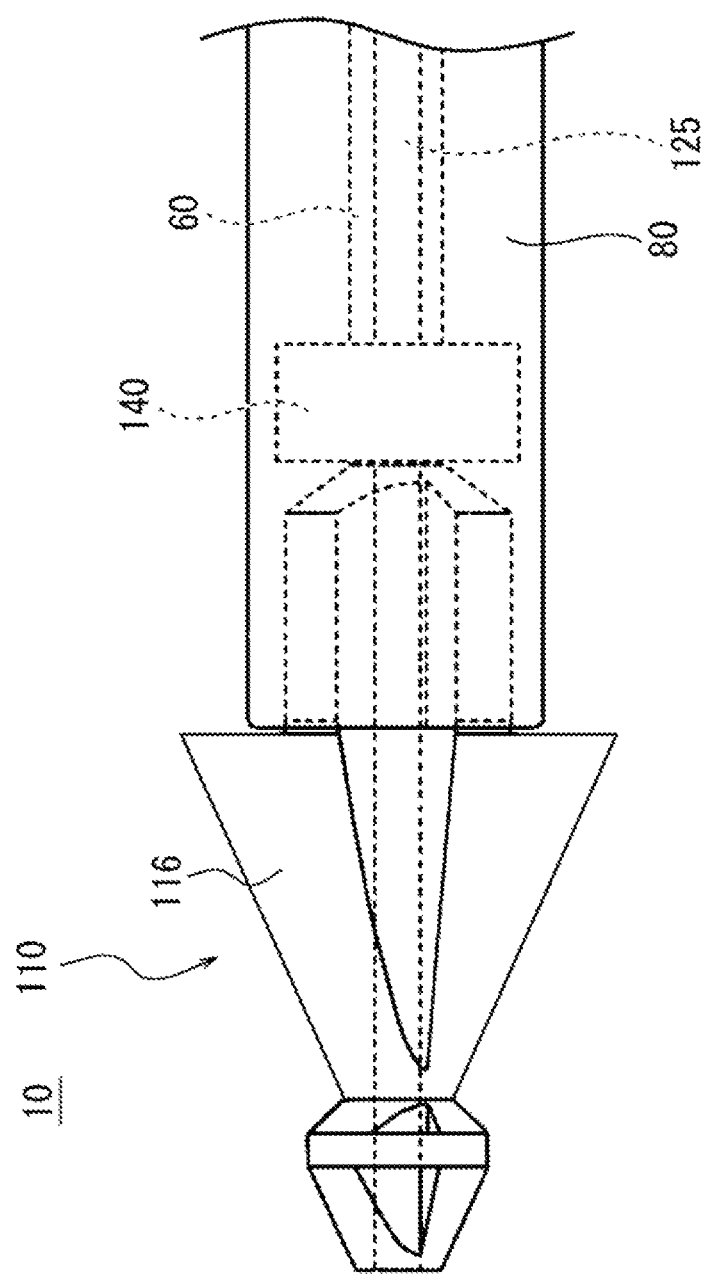
FIG. 9 is a plan view of a part including a rotation structure when a diameter of a first tapered portion is increased.

Further, in the embodiment, for example, FIGS. 2 and 4 illustrate a case in which the maximum diameter of the first tapered portion 116 is smaller than the outer diameter of the outer sheath 80, but the maximum diameter of the first tapered portion 116 may be larger than, as illustrated in FIG. 9, the outer diameter of the outer sheath 80.

Figure 10:
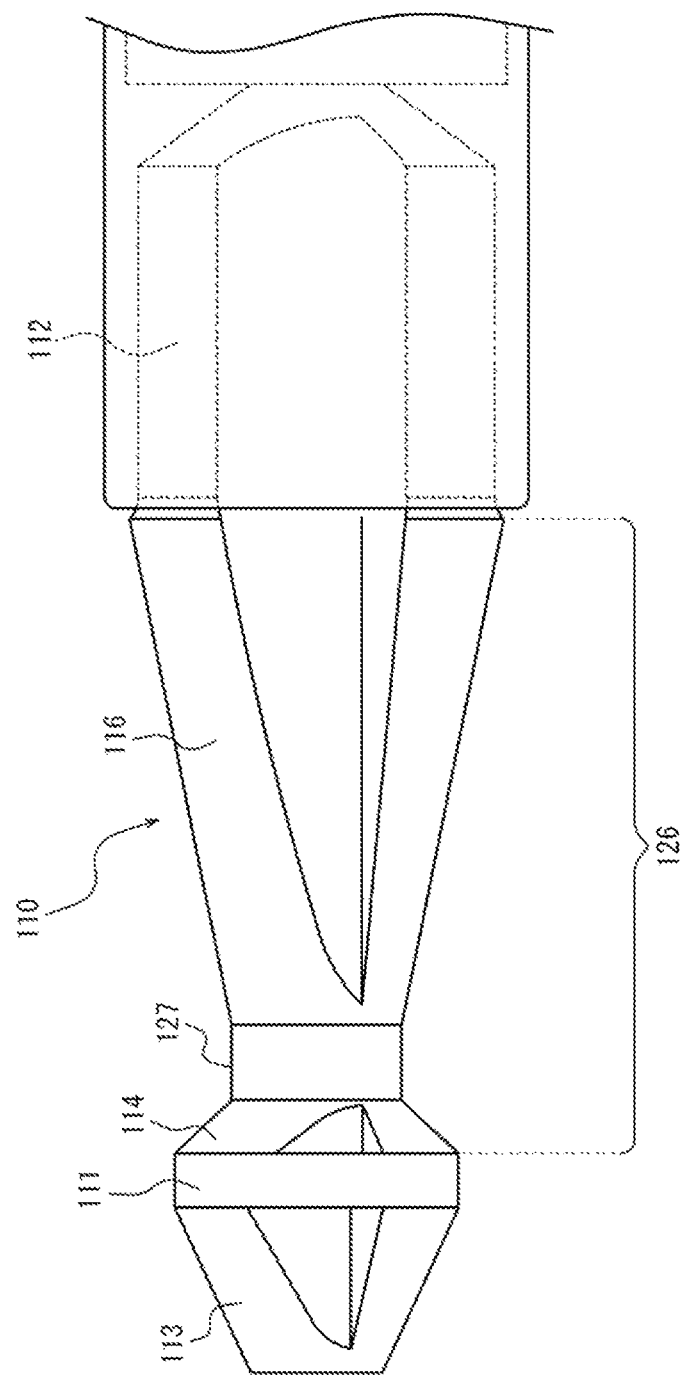
FIG. 10 is a plan view of a part including a rotation structure when a bottom portion is flat.

Further, in the embodiment, for example, FIG. 4 illustrates a configuration in which the reduced diameter portion of the first tapered portion 116 and the reduced diameter portion of the second tapered portion 114 are directly connected to each other by the bottom portion 127. However, a configuration of the bottom portion 127 connecting the first tapered portion 116 and the second tapered portion 114 to each other is not limited thereto and various configurations may be employed. For example, as illustrated in FIG. 10, the first tapered portion 116 and the second tapered portion 114 may be connected to each other through the flat bottom portion 127. At this time, abrasive grains, grinding stones, or the like may be electrodeposited on the bottom portion 127 and the surface of the bottom portion 127 may function as a cutting portion.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object in a body lumen, the medical device comprising:
   a rotatable drive shaft; and
   a rotatable rotation structure configured to be connected to a distal end of the drive shaft, the rotatable rotation structure having a proximal side and a distal side, the rotatable rotation structure including:
   an annular proximal portion;
   an annular distal portion;
   a first tapered portion having a first cutting portion, the first tapered portion decreasing in diameter toward the distal side of the rotation structure and located between the annular proximal portion and the annular distal portion, the first tapered portion including a first notch, the first notch being provided in a part of a circumferential portion of the first tapered portion, and wherein the first notch is notched in a cross-section orthogonal to an axis of the first tapered portion, and wherein a proximal circumferential portion of the first notch is greater than a distal circumferential portion of the first notch; and
   a second tapered portion having a second cutting portion, the second portion decreasing in diameter toward the distal side of the rotation structure and located distally of the annular distal portion.

2. The medical device according to claim 1, further comprising:
   a third tapered portion, the third tapered portion having a third cutting portion, the third cutting portion decreasing in diameter toward the proximal side of the rotation from the distal annular portion; and
   a bottom portion provided between the first tapered portion and the third tapered, wherein the bottom portion has an outer diameter smaller than a maximum outer diameter of the proximal portion and a maximum outer diameter of the annular distal portion.

3. The medical device according to claim 1, wherein the first tapered portion has a maximum outer diameter greater than a maximum outer diameter of the second tapered portion.

4. The medical device according to claim 1, wherein an outer diameter of the annular distal portion of the rotatable rotation structure has a is less than an outer diameter of the annular proximal portion of the rotatable rotation structure.

5. The medical device according to claim 2, wherein an angle of the third tapered portion with respect to a cross-section orthogonal to a rotation axis of the rotation structure is equal to or smaller than an angle of the first tapered portion with respect to the cross-section.

6. The medical device according to claim 1, wherein the annular distal portion of the rotatable rotation structure is a non-cutting portion capable of smoothly coming into contact with a biological tissue.

7. The medical device according to claim 1, further comprising:
   a tubular outer sheath configured to cover an outside of the drive shaft, and wherein the outer sheath is bendable.

8. The medical device according to claim 7, wherein an outer diameter of the first tapered portion is larger than an outer diameter of the outer sheath.

9. The medical device according to claim 1, wherein the first cutting portion is provided at an edge of the first notch.

10. The medical device according to claim 9, wherein the first notch is provided at two or more positions in the circumferential portion of the first tapered portion.

11. The medical device according to claim 9, wherein the second tapered portion includes a second notch, the second notch being provided in a part of a circumferential portion of the second tapered portion, and wherein the second notch is notched in a V shape in a cross-section orthogonal to an axis of the second tapered portion, and the second cutting portion being provided an edge of the second notch.

12. The medical device according to claim 2, wherein,
    the first notch is notched in a V shape in the cross-section orthogonal to the axis of the first tapered portion;
    the second tapered portion includes a second notch portion, the second notch portion being provided in a part of a circumferential portion of the second tapered portion, and wherein the second notch is notched in a V shape in a cross-section orthogonal to an axis of the second tapered portion, and the second cutting portion being provided an edge of the second notch; and
    the third tapered portion includes a third notch, the third notch being provided in a part of a circumferential portion of the third tapered, and wherein the third notch is notched in a V shape in a cross-section orthogonal to an axis of the third tapered portion, and the third cutting portion being provided at an edge portion of the third notch.

13. A medical device for cutting an object in a body lumen, the medical device comprising:
    a rotatable drive shaft;
    a rotatable rotation structure configured to be connected to the drive shaft, the rotation structure including:
    a proximal portion, the proximal portion including a cylindrical member and a plurality of connecting members surrounding the cylindrical member, each of the plurality of connecting member includes a hole portion configured to receive a bearing;
    a distal portion; and
    a constricted portion provided between the proximal portion and the distal portion, the constricted portion being separable from the proximal portion, and wherein the constricted portion includes:
    a first tapered portion having a first cutting portion, the first tapered portion decreasing in diameter toward the distal side;
    a second tapered portion having a second cutting portion, the second portion decreasing in diameter toward the proximal side; and
    a bottom portion provided between the first tapered portion and the second tapered portion; and
    one or more rings configured to surround the plurality of connecting members and the proximal portion of the rotatable rotation structure.

14. The medical device according to claim 13, wherein a distal end surface of a drive shaft is configured to adhere to a proximal end surface of the plurality of cylindrical members; and
    an outer surface of the drive shaft is configured to adhere to an inner surface of each of the plurality of connecting members such that the plurality of connecting member is configured to rotate when the drive shaft rotates and the constricted portion and the distal portion rotate when the plurality of connecting members rotate.

15. A method for cutting substances inside a body lumen using a medical device including a rotatable drive shaft, and a rotatable rotation structure configured to be connected to a distal end of the drive shaft, the rotatable rotation structure having a proximal side and a distal side, the rotatable rotation structure including: an annular proximal portion, an annular distal portion, a first tapered portion having a first cutting portion, the first tapered portion decreasing in diameter toward the distal side of the rotation structure and located between the annular proximal portion and the annular distal portion of the rotation structure and located between the annular proximal portion and the annular distal portion, the first tapered portion including a first notch, the first notch being provided in a part of a circumferential portion of the first tapered portion, and wherein the first notch is notched in a cross-section orthogonal to an axis of the first tapered portion, and wherein a proximal circumferential portion of the first notch is greater than a distal circumferential portion of the first notch, and a second tapered portion having a second cutting portion, the second portion decreasing in diameter toward the distal side of the rotation structure and located distally of the annular distal portion, the method comprising:

inserting the rotatable rotation structure into the body lumen;

moving the rotatable rotation structure in a distal direction; and cutting the substances inside the body lumen with the rotatable rotation structure during the movement of the rotatable rotation structure in the distal direction.

16. The method according to claim 15, further comprising:

moving the rotatable rotation structure in a proximal direction; and cutting the substances inside the body lumen with the rotatable rotation structure during the movement of the rotatable rotation structure in the proximal direction.

17. The method according to claim 15, wherein the medical device further includes a tubular outer sheath configured to cover an outer surface of the drive shaft, the outer sheath being bendable, the method further comprising:

bending the outer sheath at two positions; and cutting the substances inside the body lumen while the outer sheath is bent.

18. The medical device according to claim 1, wherein the first notch is notched in a V shape in the cross-section orthogonal to the axis of the first tapered portion; and wherein the second tapered portion includes a second notch, the second notch being provided in a part of a circumferential portion of the second tapered portion, and wherein the second notch is notched in a V shape in a cross-section orthogonal to the axis of the second tapered portion, and the second cutting portion being provided an edge of the second notch.

19. The medical device according to claim 18, wherein a proximal circumferential portion of the second notch is greater than a distal circumferential portion of the second notch.

20. The medical device according to claim 19, further comprising:

a third tapered portion, the third tapered portion having a third cutting portion, the third cutting portion decreasing in diameter toward the proximal side of the rotation from the distal annular portion;

a bottom portion provided between the first tapered portion and the third tapered, wherein the bottom portion has an outer diameter smaller than a maximum outer diameter of the proximal portion and a maximum outer diameter of the annular distal portion; and the third tapered portion includes a third notch, the third notch being provided in a part of a circumferential portion of the third tapered portion, and wherein the third notch is notched in a V shape in a cross-section orthogonal to an axis of the third tapered portion, and the third cutting portion being provided at an edge portion of the third notch, and wherein a proximal circumferential portion of the third notch is less than a distal circumferential portion of the third notch.

* * * * *